United States Patent [19]

Landgraf

[11] 4,237,393
[45] Dec. 2, 1980

[54] DRIVE MOTOR FOR A DENTAL HANDPIECE

[75] Inventor: Hermann Landgraf, Heppenheim, Fed. Rep. of Germany

[73] Assignee: Siemens Aktiengesellschaft, Berlin & Munich, Fed. Rep. of Germany

[21] Appl. No.: 962,717

[22] Filed: Nov. 21, 1978

Related U.S. Application Data

[63] Continuation of Ser. No. 779,100, Mar. 18, 1977, abandoned.

[30] Foreign Application Priority Data

Mar. 26, 1976 [DE] Fed. Rep. of Germany ....... 2613061

[51] Int. Cl.³ .............................................. H02K 9/00
[52] U.S. Cl. ..........................310/59; 310/47; 310/154
[58] Field of Search ...................... 310/50, 47, 41, 259, 310/154, 254, 258, 401 M, 52, 54, 58, 59, 60, 65; 32/26-28, DIG. 8

[56] References Cited

U.S. PATENT DOCUMENTS

| | | | |
|---|---|---|---|
| 1,892,997 | 1/1933 | Oldenburg | 310/60 R |
| 2,513,226 | 6/1950 | Wylie | 310/154 |
| 3,487,546 | 1/1970 | Beierlein | 32/26 |
| 3,604,960 | 9/1971 | Krestel | 310/58 |
| 3,798,775 | 3/1974 | Weinberg | 32/26 |
| 3,900,952 | 8/1975 | Landgraf | 32/27 |
| 3,936,940 | 2/1976 | Loge | 32/26 |
| 4,007,529 | 2/1977 | Fleer | 32/27 |

*Primary Examiner*—R. Skudy
*Attorney, Agent, or Firm*—Hill, Van Santen, Steadman, Chiara & Simpson

[57] ABSTRACT

A drive section for a dental handpiece having a housing with means for connection to a supply hose and means for connection to a grip section of the handpiece, the housing receiving a drive motor having a stator surrounding a rotor and at least one coolant line section extending therethrough in a direction parallel to the axis of the drive section, characterized by the stator consisting of a hard metallic material with at least one section of soft metallic material, each section being a portion of the circumference of the stator and extending the length thereof, and each section having a means for receiving a portion of the coolant line. Preferably, the stator has a cylindrical configuration in which the sections form a segment of the cylindrical configuration and are provided with a longitudinally extending bore which forms a portion of the coolant line. If the drive motor is an electrical motor, the stator has a pair of half shells of a permanent magnetic material which are separated by a pair of sections which are of soft magnetic material and act as intermediate yokes.

10 Claims, 2 Drawing Figures

DRIVE MOTOR FOR A DENTAL HANDPIECE

This is a continuation, of application Ser. No. 779,100, filed Mar. 18, 1977.

BACKGROUND OF THE INVENTION

1. Field of the Invention

The present invention is directed to a drive section for a dental handpiece such as the handpiece having a grip section with an angled piece. The drive section comprises a housing having a connection for receiving the grip section, and a connection for the supply hose and receives a drive motor having a stator surrounded by a rotor with at least one coolant line extending in an axially prarallel direction through the housing.

2. Prior Art

It has been suggested to provide a drive section for a dental handpiece in which the coolant line section is arranged between the stator and the housing of the drive section. A drive section which has the coolant line incorporated in the drive section to extend between the stator and the housing has an advantage in that no coolant lines are present on the exterior of the handpiece to interfer with the manipulation of the handpiece. However, in order to be able to house the lines within the housing of the drive section between the stator and the housing, the proposed arrangement has the disadvantage of the diameter of the motor housing being enlarged.

SUMMARY OF THE INVENTION

The present invention is directed to a drive section for a dental handpiece in which one or more coolant line sections for one or more coolant agents, which may be water, air or a mixture of air and water, are arranged in the motor housing without having to enlarge the diameter of the motor housing.

To accomplish this task, the present invention is directed to an improvement in a drive section for a dental handpiece, which drive section has a housing with means for connection to a supply hose and means for connection to a grip section of the dental handpiece, said housing receiving a drive motor having a stator surrounding a rotor and at least one coolant line section extending through the drive section in a direction parallel to the axis of the drive section. The improvements comprise the stator consisting of a hard metallic material with at least one stator section of a soft metallic material, each stator section comprising a portion of the circumference of the stator and extending the length thereof, and each stator section having means for receiving a portion of the coolant lines.

In an arrangement of the coolant line section in the improved drive section, the diameter of the motor housing need not be enlarged. In addition, contrary to other proposed structures, in which the coolant line sections would be incorporated in the stator material, which is very hard and brittle as in the case of electrical motors in which the stator material are permanent magnets, such as a ferro-magnetic material, and in the case of air motors is a hard material, the improvement of the present invention does not require any great technical resources or expenses in manufacture. When the drive motor is an electrical motor which has a permanent magnet stator, the improvement of the present invention has a particular advantage because it does not require any subsequent processing of the permanent magnet, which would impair the magnetic flux thereof. Preferably, the means for receiving a coolant line of each of the sections is a passageway or bore that extends the length of the section and each of the bores is utilized as a portion of the respective coolant line. Preferebly, the stator has a hollow cylindrical configuration and each section is a portion of the configuration with a cross section of the section being a sector of a hollow cylinder.

If the drive motor is an electrical motor, preferably two sections are arranged opposite each other and have their ends interconnected by annular end pieces or portions. The two sections and annular end pieces form a pair of spaces for receiving half shells of the permanent magnetic material of the stator. Each of the sections is of a soft magnetic material and forms an intermediate yoke extending between the two permanent magnet half shells with the lateral surfaces of the two sections and the two half shells interfitting so that the half shells and sections form the hollow cylinder of the stator.

BRIEF DESCRIPTION OF THE DRAWINGS

FIG. 3 is an exploded perspective view of the stator in accordance to the present invention.

DESCRIPTION OF THE PREFERRED EMBODIMENT

Figure 1:
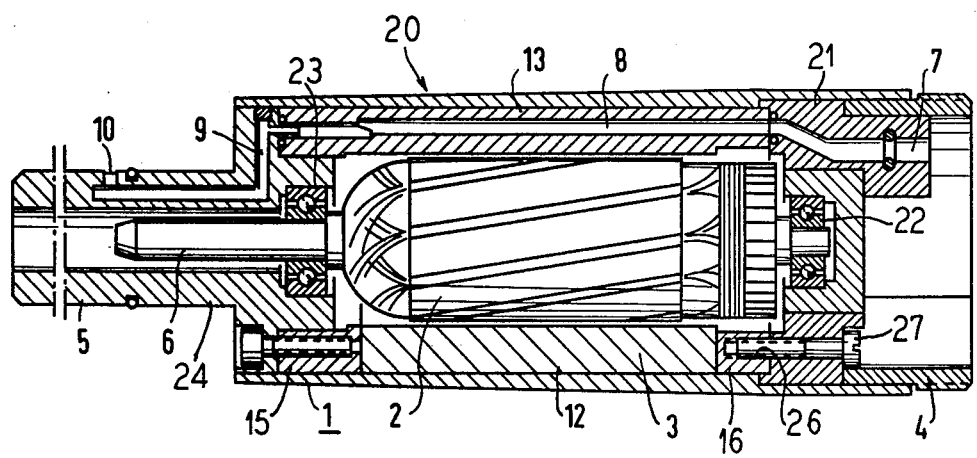
FIG. 1 is a cross-sectional view of a drive section according to the present invention taken along lines I—I of FIG. 2.

The principles of the present invention are particularly useful in a drive section generally indicated at 20 in FIG. 1 for a dental handpiece which will include a grip section and angled piece coupled to the drive section with the grip section rotatably mounting an instrument which will be driven by the motor of the drive section.

The drive section 20 has a housing 1 which receives a rotor 2 and a stationary stator 3 of a drive motor. While the drive motor is illustrated as an electrical sub-fractional horsepower motor, the housing may receive an air motor having both a rotor and stator. The housing 1 includes a rear section 4 which acts as means for connecting the drive section 20 to a supply hose, which will have at least one coolant line for either air, water, or a mixture thereof and a supply line for driving the motor such as an electrical conduit. As illustrated, the rear housing section 4 includes the annular member 21, which supports a bearing arrangement 22 that rotatably supports one end of the rotor 2 in the stator 3. In addition, the member 21 has a feed channel 7 for a cooling agent and will be provided with means (not illustrated) for applying the electrical energy in a conventional manner to the rotor 2. The opposite end of the housing 1 has a front housing section 5, which forms means for connection to the grip section. As illustrated, the front end section 5 has the bearing 23 for supporting the other end of the rotor 2 and a tubular sleeve portion 24 that surrounds the drive shaft 6 of the motor.

As illustrated, the stator 3 has a passageway bore 8 that extends substantially parallel to the axis of the rotor 2 to convey a cooling medium received from the passage or channel 7 to a radial portion of a passage 9 that extends in the tubular portion 24 of the front end section or portion 5 to a radial port 10. When the grip section is attached on the tubular sleeve portion 24 and held by conventional means such as detents, the port 10 is in communication with a ring channel provided in the grip section of the hand or angled piece so that the cooling agent may be conveyed to the head section thereof.

Figure 2:
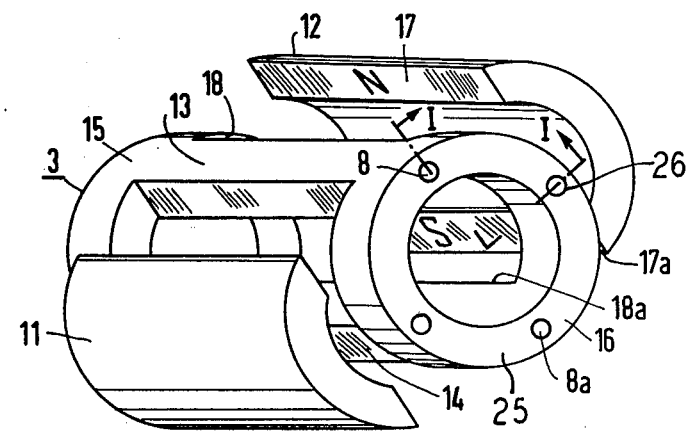

As best illustrated in FIG. 2, the stator 3 which is a permanent magnet stator, is essentially composed of two half shells 11 and 12, which are of a permanent magnetic material that consist of a ferro-magnetic material, and a body 25 of a soft magnetic (low retentivity) material which is relatively easy to work. The body 25 is formed by two diametrically opposed stator sections or portions 13 and 14 as well as two annular end pieces or portions 15 and 16. The body 25 when assembled with the two half shells 11 and 12 forms a substantially hollow stator having a hollow cylindrical configuration. In the assembled state of the stator 3, the lateral surfaces or faces 17 and 17a of the half shell 12 fit flush against a corresponding surfaces or faces 18 or 18b of the sections 13 and 14, respectively. In a similar manner, the opposite faces of the sections 13 and 14 coact with the faces of the half shell 11.

As illustrated in FIG. 1, the section 13 has a longitudinal extending or passageway bore 8 and the section 14 has a similar bore 8a (see FIG. 2). Each of the bores 8 and 8a form a portion of the respective coolant line or coolant line section. In addition to the bores 8 and 8a, each of the annular portions 15 and 16 are provided with threaded bores such as 26, which receive threaded fasteners such as 27 (FIG. 1) which attach to annular member 21 to the stator 3.

Each of the sections 13 and 14 are made of a soft magnetic material in the pull piece region to provide intermediate yokes between the half shells 11 and 12. In addition to providing the advantage of a simpler and more problem-free means for receiving the coolant lines, the sections or intermediate yokes 13 and 14, due to the low magnetic reluctance, provide an additional advantage of an improved magnetic flux guidance in the pull piece region and consequently, the stray or leakage flux of the stator field is thereby reduced.

The sections or yokes 13 and 14 are illustrated as connected to both the end pieces 15 and 16 and have a cross-sectional shape of a sector of a cylindrical member. However, they may also have a different cross-sectional shape, for example the shape of a ring segment or of a different segment of a circular ring or annulus.

While the above described embodiment was directed to an improvement in a permanent magnet stator for an electrical drive motor, the inventive improvements in the stator can also be utilized in the case of an air motor, which has a hard metal stator.

Although various minor modifications might be suggested by those versed in the art, it should be understood that I wish to employ within the scope of the patent warranted hereon, all such modifications as reasonably and properly come within the scope of my contribution to the art.

I claim:

1. In a drive section for a dental handpiece having a housing with means for connection to a supply hose and means for connection to a grip section of a dental handpiece, said housing receiving a drive motor having a stator surrounding a rotor and at least one coolant line extending through the drive section in a direction parallel to the axis of the drive section, the improvements comprising said stator consisting of a hard metallic material with at least one stator section of a soft metallic material, each stator section comprising a portion of the circumference of the stator and extending the length thereof, and at least one stator section having means for receiving a portion of a coolant line, said means for receiving being a passageway extending through the one stator section for the entire length thereof.

2. In a drive section according to claim 1, wherein each passageway comprises a longitudinal bore, each bore being a portion of the respective coolant line.

3. In a drive section according to claim 1, wherein the stator has a hollow cylindrical configuration, and wherein each section is a portion of said configuration with a cross section of a sector of a hollow cylinder.

4. In a drive section according to claim 3, wherein each passageway is a longitudinal bore, each bore being a portion of the respective coolant line.

5. In a drive section according to claim 3, wherein the stator contains two diametrically opposite stator sections, and two half shells composed of hard metallic material, each of said two stator sections and two half shells having lateral surfaces interfitting so that the half shells and stator sections form the hollow cylinder.

6. In a drive section according to claim 5, wherein the drive motor is an electric motor said stator is a permanent magnet stator, wherein said two half shells consist of permanent magnetic material and wherein the two stator sections are intermediate yokes consisting of soft magnetic material with at least one coolant line being arranged in the passageway of at least one of the yokes.

7. In a drive section according to claim 6, wherein each passageway comprises a longitudinal bore, said bore being a portion of a respective coolant line.

8. In a drive section according to claim 5, wherein the two stator sections are interconnected at their ends by a pair of annular end portions so that the half shells are received in the space defined by the pair of end portions and the two stator sections to form the hollow cylinder.

9. In a drive section according to claim 8, wherein the drive motor is an electric motor said stator is a permanent magnet stator, wherein each of the two half shells consist of a permanent magnetic material and wherein the two stator sections form intermediate yokes made of soft magnetic material and wherin the passageway for receiving a coolant line is arranged in at least one of said yokes.

10. In a drive section according to claim 1, wherein the drive motor is an electric motor said stator is a permanent magnet stator of a configuration of a hollow cylinder, said stator comprising a pair of half shells consisting of permanent magnetic material and separated by a pair of stator sections forming intermediate yokes consisting of soft magnetic material, so that the assembled yokes and half shells provide a cylindrical configuration for the hollow cylinder.

* * * * *